(12) United States Patent  
Chen et al.

(10) Patent No.: US 9,415,114 B2  
(45) Date of Patent: Aug. 16, 2016

(54) CONFORMATIONS OF DIVERGENT PEPTIDES WITH MINERAL BINDING AFFINITY

(71) Applicant: KAOHSIUNG MEDICAL UNIVERSITY, Kaohsiung (TW)

(72) Inventors: Hui-Ting Chen, Kaohsiung (TW); Kuang-Chan Hsieh, Kaohsiung (TW); Je-Ken Chang, Kaohsiung (TW); Gwo-Jaw Wang, Kaohsiung (TW); Yin-Chih Fu, Kaohsiung (TW); Mei-Ling Ho, Kaohsiung (TW); Cherng-Chyi Tzeng, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 14/805,588

(22) Filed: Jul. 22, 2015

(65) Prior Publication Data

US 2015/0320876 A1   Nov. 12, 2015

Related U.S. Application Data

(62) Division of application No. 14/317,179, filed on Jun. 27, 2014, now Pat. No. 9,314,533, which is a division of application No. 13/278,844, filed on Oct. 21, 2011, now Pat. No. 8,889,828.

(30) Foreign Application Priority Data

Apr. 21, 2011   (TW) .............................. 100113984 A

(51) Int. Cl.
| | |
|---|---|
| *A61K 47/30* | (2006.01) |
| *A61K 47/48* | (2006.01) |
| *C08G 69/48* | (2006.01) |
| *C08G 73/02* | (2006.01) |
| *C07K 5/09* | (2006.01) |
| *A61K 38/06* | (2006.01) |

(52) U.S. Cl.
CPC ........... *A61K 47/48207* (2013.01); *A61K 38/06* (2013.01); *C07K 5/0815* (2013.01); *C08G 69/48* (2013.01); *C08G 73/028* (2013.01)

(58) Field of Classification Search
None
See application file for complete search history.

(56) References Cited

U.S. PATENT DOCUMENTS

| 7,261,875 B2 | 8/2007 | Li et al. |
| 2012/0270811 A1 | 10/2012 | Chen et al. |
| 2013/0136697 A1* | 5/2013 | Kannan ............ A61K 47/48207 424/9.6 |

FOREIGN PATENT DOCUMENTS

EP   0751225 A1   1/1997

OTHER PUBLICATIONS

Hartgerink et al., "Self-Assembly and Mineralization of Peptide-Amphiphile Nanofibers," Science (2001) 294:1684-1688.
Keum et al., "Effect of anionic polyamidoamine dendrimers on the crystallization of calcium carbonate by delayed addition method," Bull. Chem. Soc. Jpn., (2003) 76:1687.
Wang et al., "Synthesis and evaluation of water-soluble polymeric bone-targeted drug delivery systems," Bioconjug Chem., (2003) 14(5):853-859.
Wang et al., "Osteotropic Peptide That Differentiates Functional Domains of the Skeleton," Bioconjugate Chem. (2007) 18:1375-1378.
Capriotti et al., "Hydroxyapatite surface-Induced Peptide Folding," J. Am. Chem. Soc., (2007) 129:5283-5287.
George et al., "Phosphorylated Proteins and Control Over apatite Nucleation, Crystal Growth, and Inhibition," Chem. Rev., (2008) 108:4670-4693.
Rimola et al., "Ab Initio Modeling of Protein/biomaterial Interactions: glycine Adsorption at Hydroxyapatite Surfaces," J. Am. Chem. Soc., (2008) 130:16181-16183.
Zaupa et al., "Origin of the Dendritic Effect in Multivalent Enzyme-Like Catalysts," J. Am. Chem. Soc., (2008) 130:5699-5709.

(Continued)

*Primary Examiner* — Christina Bradley
(74) *Attorney, Agent, or Firm* — Volpe and Koenig, P.C.

(57) ABSTRACT

A series of peptides with divergent confirmations including structures of formula (1A), (1B), (2) and (3) are provided. In the formula, wherein U, G, A, B, R1, R2 and T are as defined in the specification. The divergent peptides disclosed in the present invention are characterized in a mineral binding affinity function.

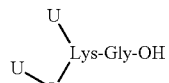

formula (1A)

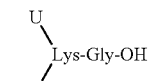

formula (1B)

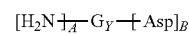

formula (2)

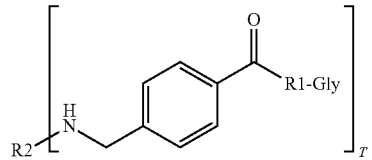

formula (3)

3 Claims, 11 Drawing Sheets

(56) References Cited

OTHER PUBLICATIONS

Almora-Barrios et al., "Density Functional Theory Study of the Binding of Glycine, Proline, and Hydroxyproline to the Hydroxyapatite (001) and (0110) Surfaces," Langmuir, (2009) 25:5018-5025.

Rosen et al., "Dendron-Mediated Self-Assembly, Disassembly, and Self-Organization of Complex System," Chem. Rev., (2009) 109:6275-6540.

Masica et al., "De Novo Design of Peptide-Calcite Biomineralization Systems," J. Am. Chem. Soc., (2010) 132:12252-12262.

Navath et al. "Amino Acid-Functionalized Dendrimers with Heterobifunctional Chemoselective Peripheral Groups for Drug Deliver Applications," Biomacromolecules (2010) vol. 11, No. 6, pp. 1544-1563.

Weisstein, Eric W. "Natural Number." from MathWorld—A Wolfram Web Resorce. http://mathworld.wolfram.com/NaturalNumber.html, downloaded Aug. 14, 2015.

U.S. Office Action issued in U.S. Appl. No. 14/317,179.

* cited by examiner

B1e

B2a G3 n = 17, p = 15
B2b G6 n = 201, p=55

B3 G3

CONFORMATIONS OF DIVERGENT PEPTIDES WITH MINERAL BINDING AFFINITY

CROSS REFERENCE TO RELATED APPLICATIONS

This application is divisional of U.S. patent application Ser. No. 14/317,179, which was filed Jun. 27, 2014, which is a divisional of U.S. patent application Ser. No. 13/278,844, filed Oct. 21, 2011 and issued as U.S. Pat. No. 8,889,828 on Nov. 18, 2014, which claims the benefit of priority to Taiwan patent application No. 100113984, filed on Apr. 21, 2011, in the Intellectual Property Office of Republic of China, the disclosure of which is incorporated by reference as if fully set forth herein.

FIELD OF THE INVENTION

The present invention relates to the divergent peptide compounds which containing aspartic acid, are advantage in chelating with calcium on biomineral to improve the potential to target biomineral.

BACKGROUND OF THE INVENTION

According to the enhancement in human living quality, the research of biomineralization is affecting the development of medical field in recent years. It includes the investigation of bone disease mechanism and the therapy strategy, remodel of teeth and treatment of oral disease, moreover, the imagination for abnormal mineralization in the body. Biomineral is a mineral product produced from organism, and contains two mainly inorganic components, carbonate and phosphate, to form hydroxylapatite (HAp) as the basic component of biomineral whose chemical composition is a crystal of $Ca_{10}(PO_4)_6(OH)_2$. In addition, there are large portions of organic components combined in biominerals.

A molecule whose possess affinity with biomineral, in general, it must has a basic structure to provide calcium binding such as polycarboxylic acid or polyphosphoric acid. After learned from the biological phenomenon, we found that an organism always secretes acid materials to offer an anion for binding with calcium in mineral, and to form biomineral in bone and teeth structure through nucleation. The structure of these acidic materials always contain carboxylic acid rich sequence originally, or derive the functional groups through posttranslational modification such as phosphorylation or sulfation to provide the ability for binding with calcium. These acidic materials may include polysaccaride, proteoglycan and protein.

In literatures, polyaspartic acid is usually to be used as an osteophilic reagent to simulate the natural protein which is rich in aspartic acid. Since polyaspartate is a known mineral binding peptide, and the length of peptide for offering affinity is usually by 6 to 12 aspartic acids. For example, Wang D. et al had published their finding at *Bioconjuate Chem.* in 2003 and 2007 to explore the comparison of different materials for bone tissue affinity and found that the repeated aspartic acids to form octapeptide presented a good affinity to bone. They conjugated the octapeptide with polymer contained fluorescent substance to observe the fluorescence accumulation in the skeletal system. Furthermore, the application in dentistry was increasing recently. For example, Liu, X.-M. et al had introduced an alendronate as a mineral targeting on cyclodextrins to be used in oral diseases.

According to Ugliengo, P.'s study, that glycine can bind with hydroxylapatite to form a stable complex by its carboxylic group and amino group. However, oxygen atoms in the protein structure play the key functional groups mainly involved in calcium binding in biological system, they may locate on the backbone of protein and water, also on the side chain of aspartic acid, glutamic acid, asparagine and phosphorylated serine. These acidic amino acids offer protein static electricity characteristic, and also affects the binding of calcium directly. The study confirmed that a proper peptide sequence not only provides the selectivity to bind with calcium, also offer biomineral a specific binding and stacking.

Since 1970, Vogtle, F. et al had designed the first synthesized globular dendrimer, which was disclosed that the character of dendrimer molecule is different from the character of a linear polymer. The dendrimer, as implied by the name, is a dendritic macromolecule polymer with a tree like structure. It is highly divergent and has accurate single molecular weight distribution. Different from the traditional linear polymer, its structure is showed in three-dimensional radial arrangement beginning from the core and extending to the outward evenly. When reaches branch point of the first layer, it is defined as the first generation. Generation is defined as the numbers of branch points from a core toward outer shell, and based on the branch point between the same layer as calculate basis. The structure from branch point to next layer is called a generation. When there are five intersection points, it represents a fifth generation dendrimer. The cartoon of dendrimer is shown in FIG. 1, if it has a core only, it will be called the zero generation, and has no intersection in such a structure.

The known dendrimer such as polyamindoamine dendrimer (PAMAM), polyester type dendrimer, polyglycerol dendrimer, triazine based dendrimer, Poly(propylene imine) dendrimer, Newkome-type dendrimers, poylylsine dendrimer, and other mixed type can be applied.

The dendrimer utilized its divergent structure characters and self-assembly behavior to achieve many performances that were much different from small molecules did. Once an interaction between single small molecule and its interaction part is not strong originally, to shorten their distance will generally be an opportunity to increase interaction. Alternatively, the poorness of interaction will be overcome by increasing numbers of the small molecules exposed to the interaction part. Therefore, the binding ability can be improved through multivalent effect of divergent molecule. Currently, there are many reports in biomaterial field including drug release, gene therapy, cell membrane penetration, cell structure controlling, and medical imagining.

In this invention, monomer aspartic acid or polyaspartate will be incorporated on divergent frameworks to assess better binding affinity. In this composition, positive charge by aspartic acid will chelate at the biomineral surface, and the divergent backbone will additionally offer multivalent binding. According to the report by Percec, V., topology arrangement that have plenty of functional groups in binding area will be a perfect approach to present aspartic acid on the surface of distributed backbone to perform divergent peptides in the present invention. It may offer more prominent mineral affinity ability because of their multivalent binding strategy.

SUMMARY OF THE INVENTION

In a biological system, collagen and acidic protein are responsible to bind biomineral such as bone by a negative function. Most of these bone binding proteins are rich in aspartic acid, glutamic acid, asparagine and phosphorylated serine. Johnson, G. A. et al and LeGeros, R. Z. were all illustrated the importance of osteopontin in the organism. Osteopontin contains polyaspartic acid in sequence, therefore, it can not only bind to bone but also react with osteocyte.

Also, polyasparatate is the most important moiety in bone delivery system when it has been proved to be capable of bone binding affinity. Due to the hydroxylapatite (HAP) structure descripted by Rimola, A. et al., HAP contains calcium ion, phosphonate and oxygen. They reported that carboxylic acid and amine group in glycine offers the functional groups to chelate with HAP crystal. Moreover, it demonstrated that helix peptide can combine to hydroxylapatite more effectively and affect this ability with varies different sequence. In this invention, the designed peptide, overcame the gap between different conformations and binding affinity, offers a specific choice in the space to the HAP surface. Additional to the binding difference produced by protein secondary structure, the present invention design divergent peptides which will provide a three-dimensional space for binding.

To survey the literatures, carboxylic acids, phosphoric acids, PAMAM dendrimer (G:1.5), diethylenetriaminepentaacetic acid (DTPA), ethylenedinitrilotetraacetic acid (EDTA) and propyleneglycolmethylether acetate (PMA) ideally provide site for calcium ion chelating. Among them, EDTA is widely utilized as a metal chelating agent. In 2003, it has ever been reported by Keum, D. K. et. al. at *Bull. Chem. Soc. Jpn.* to disclose that a half generation of polyamidoamine (PAMAM) dendrimer (G:1.5) is able to cooperate with metal. (FIG. 2A)

Zaupa, G et. al. used lysine as monomer to develop a dendritic macromolecules which provides three-dimensional skeleton. They imported a cysteine into the core of Lys dendron and used disulfide bond to complete Lys dendrimer formation. Thereafter, 1,4,7-triazacyclononane (TACN) was modified around this polymer to offer dendrimer having ability to chelate zinc ion. Due to multivalent effect, the fourth generation of Lys dendrimer with zinc ion chelation presented a significant effect in cutting ribonucleic acid (RNA). Therefore, considering space effect and multiorganization are the main reasons for promoting RNA cleavage activity.

In the past, the studies used short linear polyaspartate peptide to adopt one-dimensional interaction between polyaspartate and hydroxylapatite, however, there are many calcium ions and phohphate groups on the surface of HAP, hence, its affinity is limited to result significance, especially when the sequence is short. If we can create more interaction sites in a divergent framework to create two-dimensional orientation, it would increase the binding through cluster effect. This concept can echo with the results that Percec, V. found. They pointed out that the active functional groups binding to a same framework will generate a unit with rich multifunctional groups to perform better ability.

After careful testing and studying, the applicants with a spirit of perseverance to file this invention entitled "CONFORMATIONS OF DIVERGENT PEPTIDES WITH MINERAL BINDING AFFINITY". The applicants gain entries to a serious of peptide motifs that would be accessible providing better affinity in HAP binding, and even giving the potential advantages in biomaterial or pharmaceutical applications in the future. In this invention, we design a suitable two-dimensional binding relationship combined divergent configuration and aspartates, and develop a biomineral binding mode with the minimal arrangement to supply the insufficiencies of the prior art. The products in the present invention will include three kinds of divergent peptides. Through our thoroughly observation and understanding in the specific arrangement of ligands and analyzing biomineral binding ability by utilizing selected platforms, the mineral binding potentials of inventions will be reliably indicated.

Herein, the essential idea in the present invention "CONFORMATIONS OF DIVERGENT PEPTIDES WITH MINERAL BINDING AFFINITY" was to introduce polyamindoamine dendrimer and polylysine as the basic divergent structures, and then, to conjugate aspartic acid on them to form two- or three-dimensional ligands. It was believed to enhance binding force through cluster effect. The present invention uses the feasibility of amino and carboxyl groups on amino acid binding with hydroxylapatite, also provides positive charge to chelate with hydroxylapatite by monomer or polyasparates. In addition, a branched framework was introduced to provide the characteristics of multivalency, therefore, the invented divergent peptides will give better biomineral binding ability.

According to the idea above, the present invention provides formulas of peptides with divergent structures as formula 1A, formula 1B, formula 2 and formula 3:

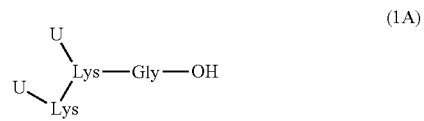

(1A)

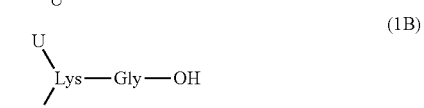

(1B)

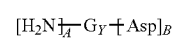 

(2)

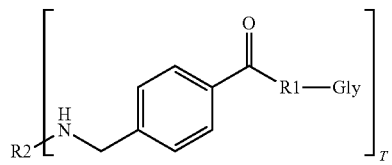

(3)

wherein U is one group selected from the following possibilities: U-Lys, -Lys-(Asp-NHAc)$_J$, —NHAc, -Lys-(Asp-)$_K$-NHAc, (Asp-NHAc)$_J$, G and R2 is the groups selected from of the following choices: a polyamindoamine dendrimer (PAMAM), a polyester type dendrimer, a polyglycerol dendrimer, a triazine based dendrimer, a poly(propyleneimine) dendrimer, a Newkome-type dendrimers and a polylysine dendrimer, R1 is -(Asp-)$_K$, the sum of A and B is $(4 \times 2^Y)$, where A, B, J, K, T and Y are natural numbers, Y is a number of generation, J is one of 1 and 2, $20 \geq K \geq 1$ and $32 \geq T \geq 1$.

Asp represents the amino acid aspartic acid, Ala represents the amino acid alanine, and Gly represents the amino acid glycine. NHAc represents N-acetyl and OH represents hydroxyl group.

Another idea in the present invention is a pharmaceutical composition including pharmaceutically acceptable carrier and an effective amount of divergent peptide with suitable conformation. The composition is processed by pharmaceutical preparation method, it can make from any dosage appropriate to feed mammalian body and have medical functions as aforesaid. The mammalian is human or mammalian called in biology.

Another idea in this invention "CONFORMATIONS OF DIVERGENT PEPTIDES WITH MINERAL BINDING AFFINITY" is to obtain the molecules with three-dimensional conformation for the following applications and modifications through stepwise synthetic steps, accordingly, their size can be ideally controlled and multifunctional groups on molecular surface can be installed. To compare to linear macromolecules in the prior art, these divergent peptide macromolecules have several characteristics below: (1) stable structure and small particle; (2) controllable hydrophilicity and hydrophobicity; (3) globule-like structure; (4) according to different generation to regulate their size and conformation.

To achieve the ideas above, the present invention will obtain the molecule with programmable size, three-dimensional arrangement, and multifunctional groups through synthetic steps. Dendrimers are well known in a serious of biomedical applications, but there are rare finding concerning in biomineral binding. The linear aspartic acid peptide L1b which has binding ability with hydroxylapatite is as the reference component here, (FIG. 3) however, the appropriate number or arrangement of aspartate in the molecule have not been disclosed yet. The divergent peptide macromolecules which are developed by the present invention can provide the arrangement in three-dimensional radial orientation, increase binding ability through multivalency, and create binding chances by rich multifunctional groups in the area.

According to the researches reported by Almora-Borrios, N. et al and Capriotti, L. A. et al, the peptide with a secondary structure is more contributive to mineral affinity such as another reference component, L1a. In addition, George, A. et al have published a finding on *Chem. Rev.* in 2008 to mention short peptides, which sequence contained continuous 6-12 aspartic acids similar to reference component L1b, presented significant bond affinity ability. In the prior art, linear polyaspartate produced almost one-dimensional binding relationship with mineral. However, there are many calcium and phosphate ions existed on hydroxylapatite surface. It inferred that the affinity of linear peptide is limited. If the interaction ligands can be arranged into a two-dimension, the binding force will be able to enhance through cluster effect. At the same time, Masica, D. L. et al also reported their idea on *J. Am. Chem. Soc.* in 2010. They illustrated the key groups on studied protein should be arranged to reach the interaction site on HAp appropriately, thereafter, the affinity between protein and HAp was enhanced. Therefore, the present invention uses L1a and L1b as references, (FIG. 3) and designs divergent peptides based on L1b to assess the appropriate distance for divergent peptides binding on hydroxylapatite.

According to $A+B=4\times2^Y$, when the sum of A and B is 32, the divergent peptide is a third generation structure, and its diameter is about 4 nm. The sum of A and B is 64, the divergent peptide is a fourth generation structure and the diameter is around 5 nm. The sum of A and B is 128, the divergent peptide is a fifth generation structure and the diameter is about 6 nm. The sum of A and B is 256, the divergent peptide is sixth generation structure and the diameter is about 7 nm. The R1 in formula 3 represents $-(Asp-)_K$, wherein the K value is the numbers of connected Asp. Although it has reported that the peptide containing 8-12 aspartic acids has good affinity with bone, the mineral affinity ability can be suggested by the retention time in hydroxylapatite column As data shown in Table 1, the retention time of tested compounds in the present invention is distributed in 12, 13 and 14 minutes.

TABLE 1

Retention time in hydroxylapatite column test

| compound | retention time (min) |
|---|---|
| B3 | 12.5 |
| L1c [SEQ ID NO: 3] | 13.0 |
| L1b [SEQ ID NO: 2] | 13.3 |
| L1a [SEQ ID NO: 1] | 13.5 |
| B1c | 13.6 |
| B2a | 13.8 |
| B2b | 13.9 |
| B1b | 14.0 |
| B1a | 14.1 |
| B1d | 14.5 |

The linear peptide, reference component L1b, which possesses mineral affinity ability, is already known in literature. Its structure is HO-Gly-(Asp)$_6$-NHAc [SEQ ID NO: 2] and retention time is 13.3 minutes. Linear L1c produced in the present invention belongs to formula 1B and has structure H$_2$N-(Gly)$_3$-(Asp)$_3$-NHAc [SEQ ID NO: 3] and its retention time is 13.0 minutes. The number of aspartic acid in L1c is only half of that in L1b, but the retention time of L1c is 13.0 minutes and is slightly different from 13.3 minutes that L1b has.

Although the linear reference component L1a does not have the functional group (carboxyl group) which can bind with calcium, its secondary helix structure still can provide excellent binding ability because its retention time can reach 13.5 minutes. Therefore, it confirms that structure arrangement is more contributive than continuous aspartic acids in hydroxylapatite binding.

After compared the retention time in HAP chromatography for divergent peptides in formula 1A, we found: (1) Compared the binding difference in same generation. Compound B1b binds 2 aspartic acids on each branch did not perform significant enhancement in mineral affinity when it was compared with compound B1a which contains single aspartic acid on each branch. (2) Compared the binding difference in same amount of binding motifs. B1c and B1d peptides in formula 1A contain lysine dendrimer with backbone (HO-Gly-Lys- - -Asp-HNAc). B1c is a second generation dendrimer and has 4 divergent branches, alternatively, B1d is a third generation dendrimer and has 8 divergent branches. Both B1c and B1d compounds contain totally 8 carboxylic acids on their backbone but the retention times are 14.1 and 13.9 minutes, respectively. (Table 1) Obviously, B1d includes more branches, and presents better binding affinity.

Among compounds in formula 2, B2a is a third generation polyamindoamine dendrimer (PAMAM) with 32 branches and performed 14.1 minutes in retention, B2b is the sixth generation with 256 branches and performed 13.9 minutes in retention. Relied on the identification, the amounts of aspartic acid on B2a and B2b are determined as 15 and 55, and their modified ratio were 46% and 21% based on surface branches, respectively. Obviously, both of them present stronger binding ability compared to reference component L1b (13.3 minutes). It shows multidivergent arrangement can increase the ability of binding with hydroxylapatite.

Compound B3 in formula 3 is formed by coupled the reference component L1b ((Asp)$_6$-Gly-OH) [SEQ ID NO: 2] with a third generation backbone (16 branches). Compared to B2a which is with the same generation backbone but modified by 15 aspartic acids, the retention time shows 12.5 minutes for B3 and 14.1 minutes for B2a, but reference component L1b is 13.3 minutes. Each branch of compound B2a modified single aspartic acid only, but each branch of compound B3 and L1b included 6 aspartic acids. Apparently, to arrange enough aspartates in the divergent skeleton like compound B2a will offer better hydroxylapatite binding ability. In principle, the K value represents the total number of aspartic acid (Asp) in the molecules and can reach 50 or 100 even higher. However, considered the binding ability of aspartic acid, the apropos K value is $20 \geq K \geq 1$, the recommended one is $15 \geq K \geq 1$. The T value is changed with the generation, but synthesis dependence will lead the generation number $\geq T$ value, theoretically.

GENT PEPTIDES WITH MINERAL BINDING AFFINITY" are carried out by the modified solid phase peptide synthesis. (scheme 1) Several steps are included below: (1) selected a appropriated resin as a original material, then soaked in organic solvent; (2) used a deprotection reagent (DEP) to remove fluorenylmethyloxycarbonyl (Fmoc), a N-terminal protecting group; (3) added amino acid and coupling agent such as benzotriazole-1-yl-oxytrispyrrol-idino-phospghonium hexafluoro-phosate (PyBOP), and then coupled in active reagent (ACT); (4) after the reaction is finished, capping reagent (CAP) is added to terminate residual amino group on resin; (5) repeated the step 2, 3 and 4 above.

Scheme 1

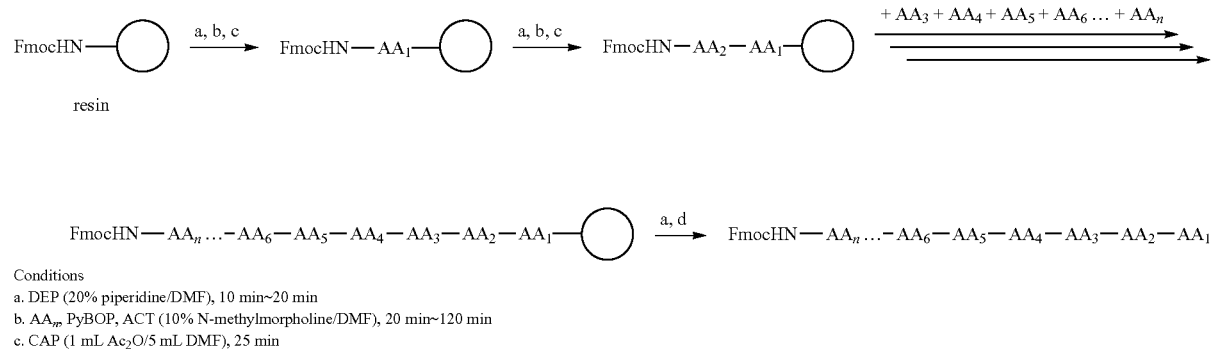

Conditions
a. DEP (20% piperidine/DMF), 10 min~20 min
b. $AA_n$, PyBOP, ACT (10% N-methylmorpholine/DMF), 20 min~120 min
c. CAP (1 mL Ac$_2$O/5 mL DMF), 25 min
d. TFA/H$_2$O The backbone of the formula 2 and the formula 3 can use same dendrimer such as polyamindoamine dendrimer. The sum of A and B in formula 2 and the largest T value in formula 3 all represents the numbers of surface functional group in every generation, wherein the B and T value represents modified number, so $A+B \geq T \geq 1$.

Accordingly, another idea in "CONFORMATIONS OF DIVERGENT PEPTIDES WITH MINERAL BINDING AFFINITY" is to increase binding ability between molecules by multivalency and multiple bonding. Consequently, the applications of divergent peptides in biomedical materials will include drug releasing, gene therapy, cell membrane penetrating, cell structure controlling and medical imagining. Hence, the divergent peptide conformation can achieve more striking mineral affinity ability because of the multivalent bonding effect.

In the present invention "CONFORMATIONS OF DIVERGENT PEPTIDES WITH MINERAL BINDING AFFINITY", the G value of the formula 2 and R2 of the formula 3 represent polyamindoamine dendrimer (PAMAM). According to the ideas above, known dendrimers in literatures can be used to prepare the divergent peptides followed the experiments in this invention, for example, polyester type dendrimer developed by Frechet, polyglycerol dendrimer by Frey and Haag, triazine based dendrimer by Simanek, poly(proplyeneimine) dendrimer, newkome-type dendrimer, polylysine dendrimer and other types. Among them, polyamindoamine dendrimer (PAMAM), polypropyleneimine dendrimer and polylysine dendrimer are more suitable for utilizing directly. If the surface groups is not amino group (—NH$_2$) in other type or mixed type dendrimers, some chemical modification should need in prior use.

According to the ideas above, the preparation of peptides in the present invention "CONFORMATIONS OF DIVER- The synthetic materials can utilize commercially available products such as N-9-fluorenylmethyloxycarbonyl-alanine (Fmoc-Ala-OH), Fmoc-Lys(Boc)-OH, Fmoc-Asp(tBu)-OH, Fmoc-Lys(ivDde)-OH, Fmoc-Lys(Fmoc)-OH and 4-carboxybenzaldegyde, for obtaining divergent peptides.

N,N-dimethylformamide (DMF) and other hydrophobic solvents are used as organic solvents to soak resin. The level of reaction is confirmed by Kaiser test. After reaction finished, using capping reagent (CAP) to terminate the incomplete reaction on resin. Depends on the length of sequence and the property of amino acid, the operation time of the deprotection and coupling are varies, in addition, couple repeats may need for coupling reaction above to obtain the desired peptide compounds.

To study three-dimensional conformation and multivalent effect for divergent peptides, the present invention developed different generations of lysine dendrimer and purchased polyamindoamine dendrimer (from generation 3 to generation 6) to synthesize compound B1a, B1b, B1c and B1d in formula 1A, compound B1e in formula 1B, compound B2a, B2b in formula 2 and compound B3 in formula 3. There is aspartic acid modification on N-terminal (—NH$_2$) of their backbone. (FIGS. 2B to 2F)

The synthesis of reference component L1a used N-9-fluorenylmethyloxycarbonyl-alanine (Fmoc-Ala-OH) as the amino material and followed scheme 1 to connected 6 alanines on the sequence sequentially to obtain product 2. The reaction time is prolonged by increased the number of alanine. After deprotection and acetylation, compound 3 was obtained. Finally, L1a was given after free peptide from resin by 95% trifluoro acetic acid (TFA) cleavage. (Scheme 2)

Scheme 2

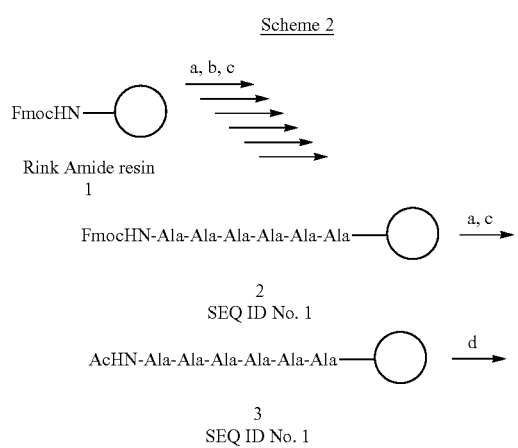

conditions:
a. DEP, 5 min × 2;
b. ACT, PyBOP, Fmoc-Ala-OH;
c. CAP, 25 min;
d. 95% TFA/H₂O The way to synthesize L1b follows the synthetic approach of L1a, as shown in Scheme 3. Using preloaded Fmoc-Glycine Wang resin, after removing the protecting group, coupled with Fmoc-Asp, synthesized 6 Asp on the sequence continuously and obtained product 5. After that, remove the peptide from resin conjugation by 95% TFA to obtain L1b.

Scheme 3

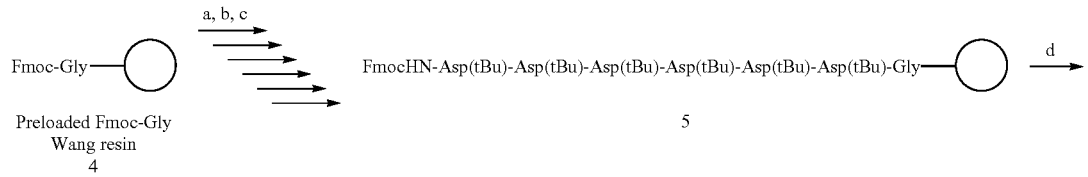

AcHN-Asp-Asp-Asp-Asp-Asp-Asp-Gly-OH

L1b
SEQ ID No. 2 conditions:
a. DEP, 5 min × 2;
b. ACT, PyBOP, Fmoc-Asp(tBu)-OH;
c. CAP, 25 min: d. 95% TFA/H₂O According to the steps above, it was stepwise coupled three times with Fmoc-Gly-OH and three times with Fmoc-Asp(tBu)-OH, then removed the solid supports to obtains compound L1c. (Scheme 4)

Scheme 4

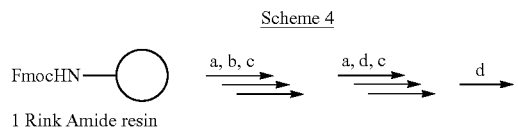

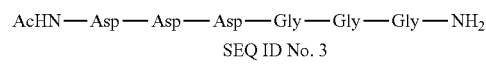

AcHN—Asp—Asp—Asp—Gly—Gly—Gly—NH₂
SEQ ID No. 3
L1c conditions:
a. DEP, 5 min x 2; b. ACT, PyBOP, Fmoc-Gly-OH;
c. CAP, 25 min;
d. ACT, PyBOP, Fmoc-Asp(tBu)-OH
e. 95% TFA/H₂O Preparations of formula 1A and 1B in the present invention "CONFORMATIONS OF DIVERGENT PEPTIDES WITH MINERAL BINDING AFFINITY" are modified from the typical peptide synthesis (Scheme 1).

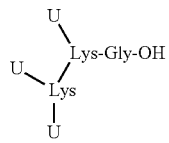

Formula 1A

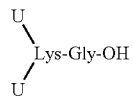

Formula 1B

As shown in Scheme 5-1, Fmoc-Lys(ivDde)-OH was firstly coupled on resin to obtain compound 6, then, its Fmoc protecting group was removed before it coupled with Fmoc-Lys(Fmoc)-OH to obtain product 7 which contains two Fmoc protecting groups to generate the first ramification. Consequently, it was coupled with Fmoc-Asp(tBu)-OH and obtained product 8. After removing protecting group and resin, B1a was offered.

Scheme 5-1

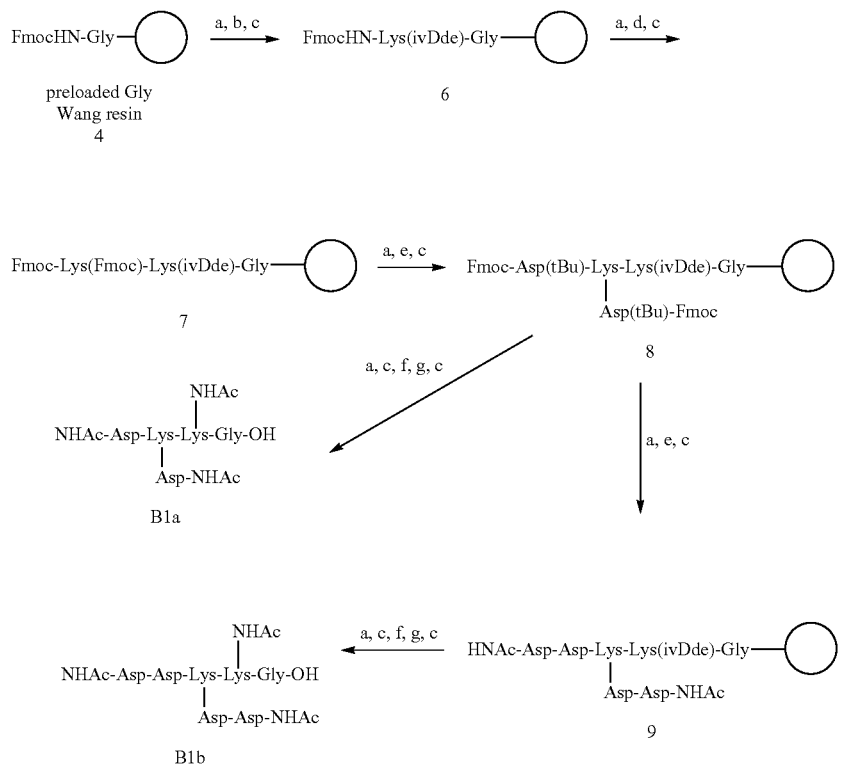

Conditions:
a. DEP 5 min × 2;
b. ACT, PyBOP, Fmoc-Lys(ivDde)-OH;
c. CAP, 25 min;
d. ACT, PyBOP, Fmoc-Lys(Fmoc)-OH;
e. ACT, PyBOP, Fmoc-Asp(tBu)-OH;
f. 4% hydrazine/DMF, 10 min × 2;
g. 95% TFA/H$_2$O;

If it needs to increase the number of Asp, it can repeat the synthetic steps as mentioned. After removing Fmoc on compound 8, Fmoc-Asp(tBu)-OH was coupled continuously to obtain B1b with di-aspartate in each branch.

If one or more branches is needed, after remove Fmoc of compound 7, the next generation of divergent backbone can be synthesized by coupled with Fmoc-Lys(Fmoc)-OH as shown in Scheme 5-2. And continuously repeated this reaction, varies generations of divergent lysine dendrimer backbone can be generated. According to the necessity, every branch was modified by 1-2 Fmoc-Asp(tBu)-OH by following the similar procedures above, then, polyaspartate dendrimers which constructed on lysine backbone were obtained such as compound B1c and B1d.

Scheme 5-2

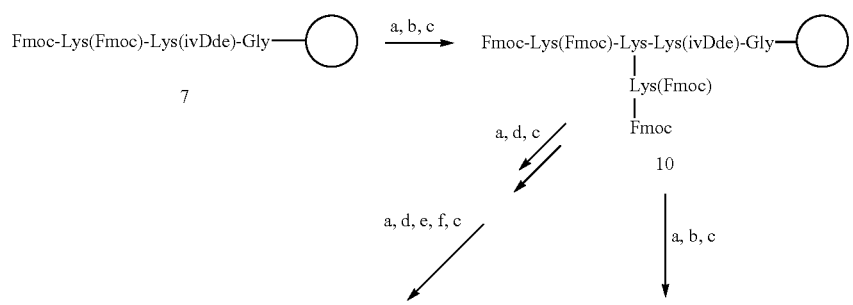

-continued

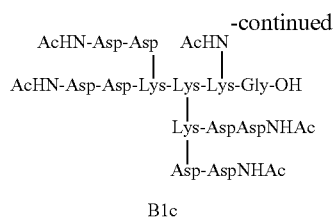

B1c

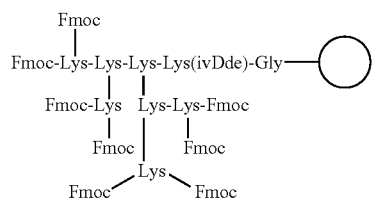

11 ↓ a, d, c

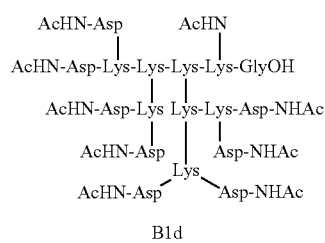

B1d

←—— a, d, e, f, c ——

Conditions:
a. DEP, 5 min × 2;
b. ACT, PyBOP, Fmoc-Lys(Fmoc)-OH;
c. CAP, 25 min;
d. ACT, PyBOP, Fmoc-Asp(tBu)-OH;
e. 4% hydrazine/DMF, 10 min × 2;
f. 95% TFA/H₂O;

In Scheme 5-1 and 5-2, if it uses lysine with different or same protecting groups on its side chain and N-terminal, it will obtain single or a pair of addition products. For example, to use Fmoc-Lys(Fmoc)-OH can remove both side chain and N-terminal protecting group under piperidine treatment, then, can obtain a pair of adducts on lysine in formula 1 B, and also can obtain single addition such as formula 1A by control equivalent number. When Fmoc-Lys(ivDde)-OH used, its Fmoc and ivDde groups will respectively remove by piperidine and hydrazine, to obtain single addition in each site. In homogenous liquid phase, peptides in formula (2) can be prepared.

Formula (2)

To make the reaction completely, imported a microwave system to help synthesizing compound B2a and B2b. Mixed different generations of PAMAM and Fmoc-Asp(tBu)-OH and reacted in N-methyl morpholine DMF solution for 5 hours. After removed all protecting groups, dialysis membrane (MWCO 35000) was used for purification. The crude product was further purified by Sephadex G50 gel filtration chromatography. A yellow oily compound B2a was eluted by used water as mobile phase. Followed the precedent of B2a synthesis and purification, it can obtain compound B2b by microwave radiation for 9 hours.

Another idea in the present invention is to prepare a polyamindoamine dendrimer which contains short polyaspartate peptide. The structure of the divergent peptide was shown in formula 3. Its synthesis is mentioned below. First, prepared peptide 5 which contained 6-repeat aspartic acid. Then, removed Fmoc protecting group of product 5, connected 4-carboxylbenzaldehyde with the peptide, and reacted with the third generation of polyamindoamine dendrimer. Finally, free peptide from resin and obtained compound B3.

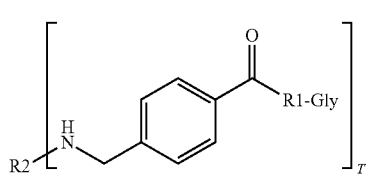

Formula 3

The purities of final products in the present invention are all determined by High-Performance Liquid Chromatography and identified its structure by Mass spectrophotometer and Nuclear Magnetic Resonance spectrophotometer. For example, the identification of compound B3 can be carried out by H-NMR spectrum. It displayed that no aldehyde signal was observed between 10-8 ppm, two doublet splits between 8-7 ppm were considered as hydrogen signals on disubstituted benzene, polyamindoamine dendrimer signals was told between 3.2-2.8 ppm, and a signal of beta-hydrogen on aspartic acid was located between 2.8~2.6 ppm.

According to the ideas above, oligopeptide derivatives in the present invention can produce a pharmaceutical composition, which is composed with pharmaceutical carriers, adjuvant, diluents, excipients or solvents, accepted by bodies and provided curative effect when medicating into bodies. The polypeptide aforesaid can used a traditional method to produce the form of a drug which is provided different taking routes to use, such as the pharmaceutical composition can arrived to medicinal part directly. The form of a drug is determined by medicating route, prescription property, disease condition, patient's body type, weight, surface area, age and sex, and other drug compatibility. The effect of pharmaceutical composition can preliminary assessment in vitro, then medicated to animals to assess the effect of the composition at medicinal part.

The excipients aforesaid or called "pharmaceutically acceptable carriers or excipients" and "bioavailability carriers or excipients" include any appropriate compounds known to be used for preparing the dosage form, such as solvents, dispersants, coatings, antibacterial or antifungal agents, preserved or delayed absorbents. The kind of carriers or excipients usually does not have activity of treating disease. Each formulation produced by combining the derivatives disclosed in the present invention and the pharmaceutically acceptable carriers or excipients will not produce adverse reactions, allergy or other inappropriate reactions when medicated to animals and humans. Hence, the derivatives disclosed in the present invention with the pharmaceutically acceptable carriers or excipients are suitable for clinical and human. The dosage of the present invention compounds can reach treatment effect by medicating in venous, oral and inhaled or via a part of nose, rectal, vaginal, or sublingual routes.

The carrier is different with each formulation, the sterile injection components can be the dissolved or suspended in the non-toxic intravenous injection diluents or solvents, such as 1,3-butanediol, and the available carriers are mannitol or water. Besides, the fixed oil or mono- or di-nucleotide oil ester suspension medium using in synthesis are the commonly used solvent. The fatty acid such as oleic acid, olive oil or castor oil and its nucleotide oil ester derivatives, especially the form through polyoxy-ethylation all can produce the injection agent and are pharmaceutically acceptable oil. Such oil solution or suspension may include long-chain alcohol diluents or dispersants, carboxyl methyl cellulose or similar dispersants. Other carriers are common surfactant such as Tween, Spans or other analogous emulsion, or the pharmaceutically acceptable solid, liquid or other bioavailability enhancing agent used for developing the formulation that used in the pharmaceutical industry.

The composition for oral administration adopts any oral acceptable formulation, which includes capsule, pastille, tablet, emulsion, liquid suspension, dispersant and solvent. The carrier generally used in the oral formulation, taking the pastille as an example, the carrier may be a lactose, a cornstarch, a lubricant, such as magnesium stearate is a basic additive. The diluents used in capsule including lactose and dried cornstarch. For preparing the liquid suspension or emulsifier formulation in an oil interface in combination with the emulsion or the suspending agent, and the appropriate amount of the sweetening agent, the flavoring agent or the pigment is added as needed.

The components of nasal aerosol or inhalation can produce by the pharmaceutical manufacturing technology. For example, dissolved the component into normal saline and add benzyl alcohol or other appropriate preservatives or absorbefacient to enhance bioavailability. The components of the present invention compounds can produce as a suppository to medicate through rectum or vagina.

The compound of the present invention can also be administered intravenously, as well as subcutaneously, parentally, muscular, or by the intra-articular, intracranial, intra-articular fluid and intra-spinal injection, the sterna injection, the intraspinal injections, the aortic injection, the sterna injection, the intra-lesion injection or other appropriate administrations.

Therefore, the present invention is truly a rare novel invention and industrial applicable, and application according to the law.

Other objects, advantages and efficacy of the present invention will be described in detail below taken from the preferred embodiments with reference to the accompanying drawings, in which:

EXPERIMENTAL MATERIALS AND METHODS

Figure 1:
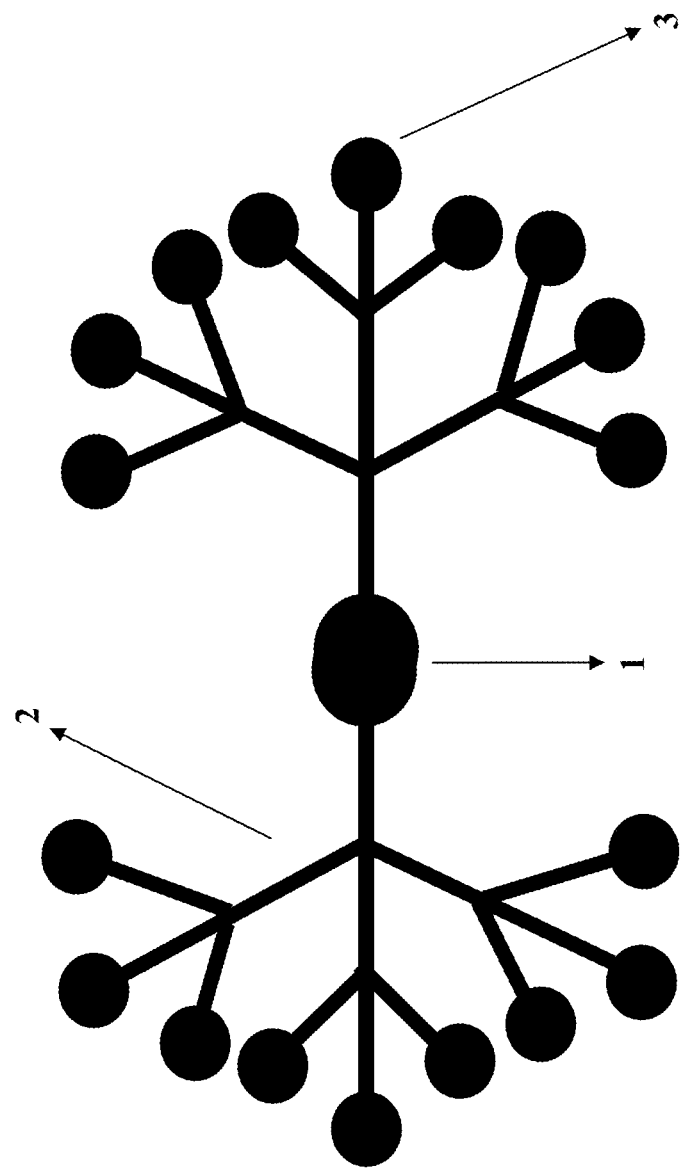
FIG. 1 shows the dendrimer: 1. core, 2. branch site, 3. terminal functional group.
Figure 2A:
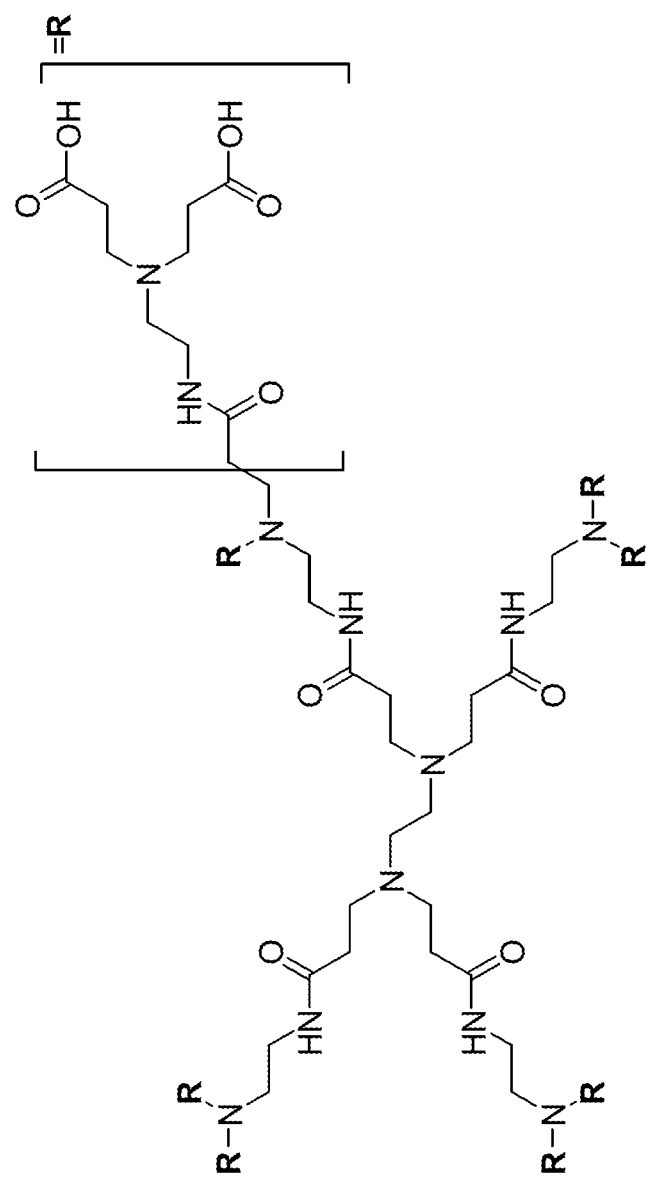
FIG. 2A shows the 1.5 generation of dendrimer.
Figure 2B:
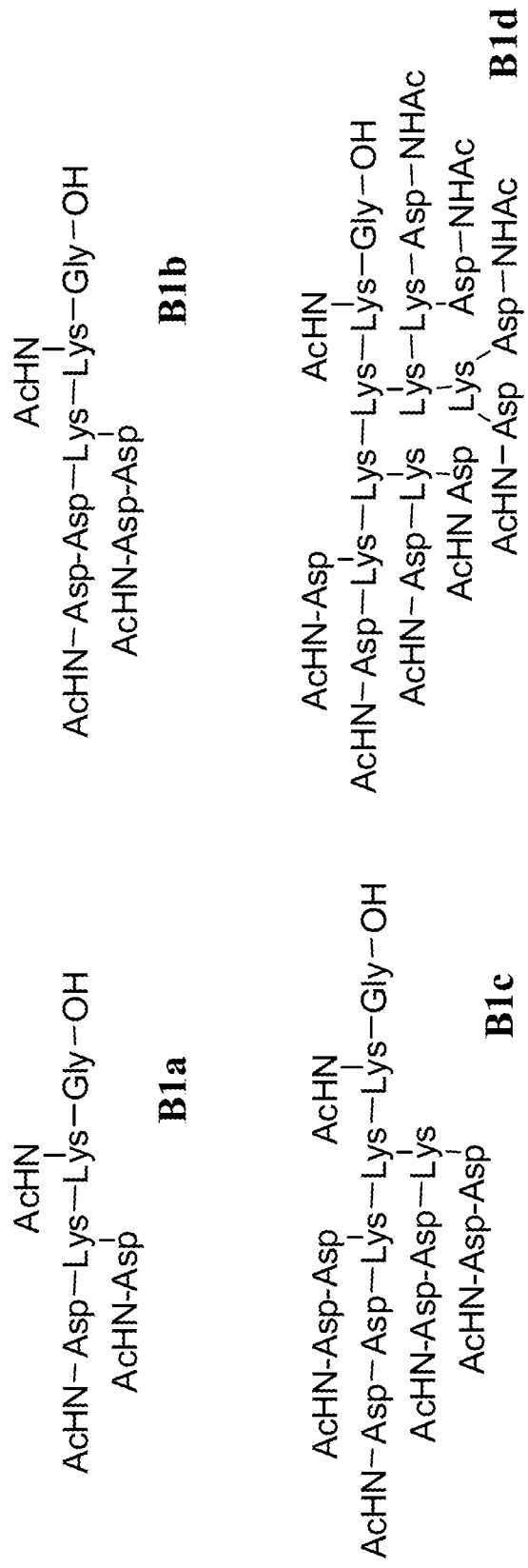
FIG. 2B shows compounds in formula 1A.
Figure 2C:
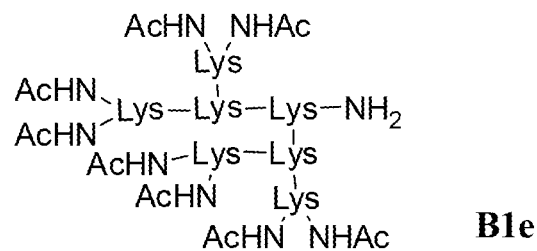
FIG. 2C shows the compound in formula 1B.
Figure 2D:
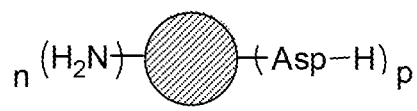
FIG. 2D shows the compound in formula 2.
Figure 2E:
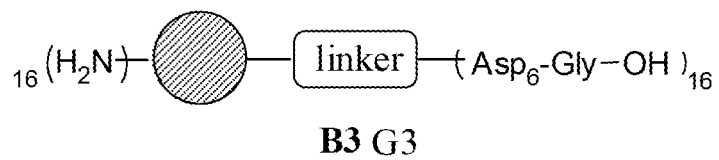
FIG. 2E shows the compound in formula 3.
Figure 2F:
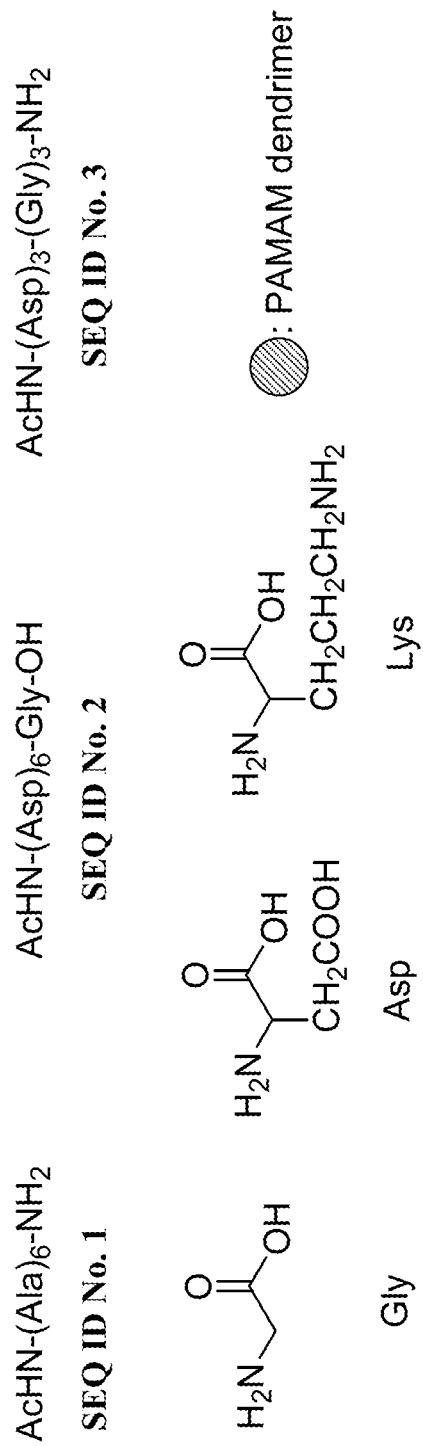
FIG. 2F shows the reference components.
Figure 3:
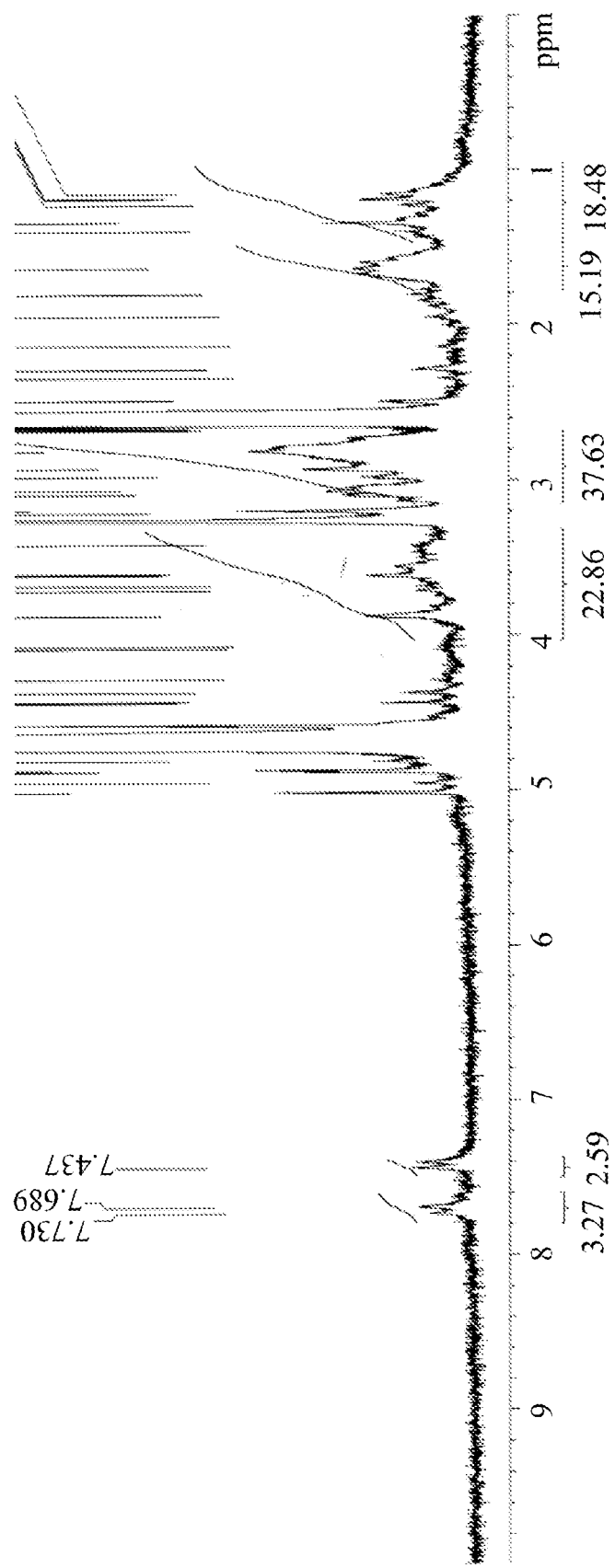
FIG. 3 shows the Hydrogen Nuclear Magnetic Resonance (H-NMR) spectrum of compound B3: the magnetic field is 200 MHz, the solvent is Deuterium oxide ($D_2O$).

The present invention will now be described more specifically with reference to the following embodiments. It is to be noted that the following descriptions of preferred embodiments of this invention are presented herein for purposes of illustration and description only; it is not intended to be exhaustive or to be limited to the precise form disclosed.

The present application "CONFORMATIONS OF DIVERGENT PEPTIDES WITH MINERAL BINDING AFFINITY" will be fully understood from the following embodiments, and thereby being accomplished based thereon by one skilled in the art. However, the practice of the present application is not intended to limit to the following embodiments in its practice, and the skilled person can still conduct other embodiments according to the spirit of embodiments presented herein that belong to the scope of this invention.

I. Chemicals and Equipments

The common chemicals were purchased from TEDIA, ACROS or Merck Chemcals. All chemicals have not been purified unless have special note. All amino acid, benzotriazole-1-yl-oxytrispyrrol-idinophospghonium hexafluorophosate (PyBOP) and preloaded Glycine Wang resin were purchased from Novabiochem. The polyamindoamine dendrimer(PAMAM) was purchased from Dendritech. The second type Hydroxylapatite which particle size is 20 μm, was purchased from Bio-Rad. Reverse-Phase Thin-Layer Chromatography (RP-TLC) plates were purchased from Merck Chemicals. Both LH20 and G75 gel as stationary phase of Liquid Chromatograghy (LC) were purchased from GE Healthcare. Used Varian's 400 MHz Nuclear Magnetic Resonance (NMR) to analyze products. Used Bruker's Autoflex III MALDI-TOF/MS Spectra to identify molecular weight of products. Used Agilent's 1100 series High Performance Liquid Chromatography (HPLC) with $C_5$ reversed phase column to analyze the purity of products.

II. Amino Acids and Linker Used in the Experiments

Fmoc-Ala-OH, Fmoc-Lys(Boc)-OH, Fmoc-Lys(ivDde)-OH, Fmoc-Lys(Fmoc)-OH, 4-carboxybenzaldehyde.

III. Reagent Preparation

The deprotection reagent (called DEP) contains 20% piperidine in N,N-dimethylformamide (DMF).

The activation reagent (called ACT) is prepared as 10% N-methylmorpholine in N,N-dimethylformamide (DMF).

The capping reagent (called CAP) is prepared from 5 mL of N,N-dimethylformamide (DMF) and 0.1 mL of acetic anhydride ($Ac_2O$).

The Kaiser test also called amino test or ninhydrin test. The staining solution is used 0.28M ninhydrin in ethanol, pyridine, and 42.4M phenol in ethanol. All the three solutions were proportional added into the resin, and the mixture was heated to 120° C. to monitor the color change. Thus, resins or solution appear as blue or purple presents for the presence of amine group. Contrariwise, appearance of yellowish presents is fairly trace of amine group. Except the special instruction, the color presents in Fmoc-removing step represents completed reaction when it appears blue or purple, and when it shows yellowish presents represents success in coupling step.

Hydroxylapatite Column Test

Figure 6:
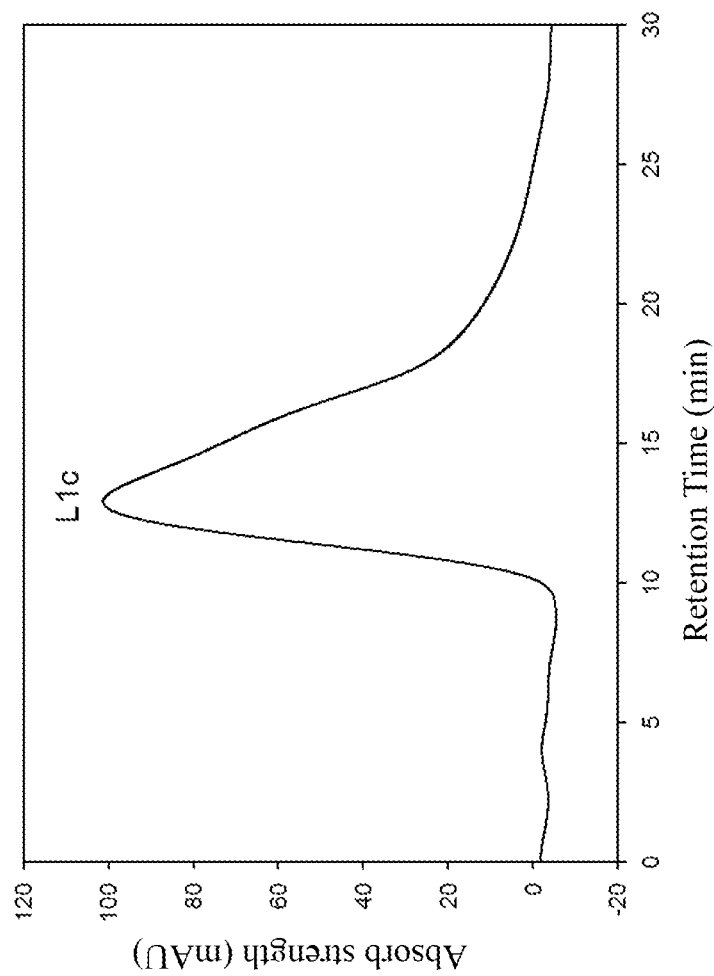
FIG. 6 shows the retention time of compound L1c in hydroxylapatite (HAp) column: the X-axis is retention time, the Y-axis is relative strength.
Figure 7:
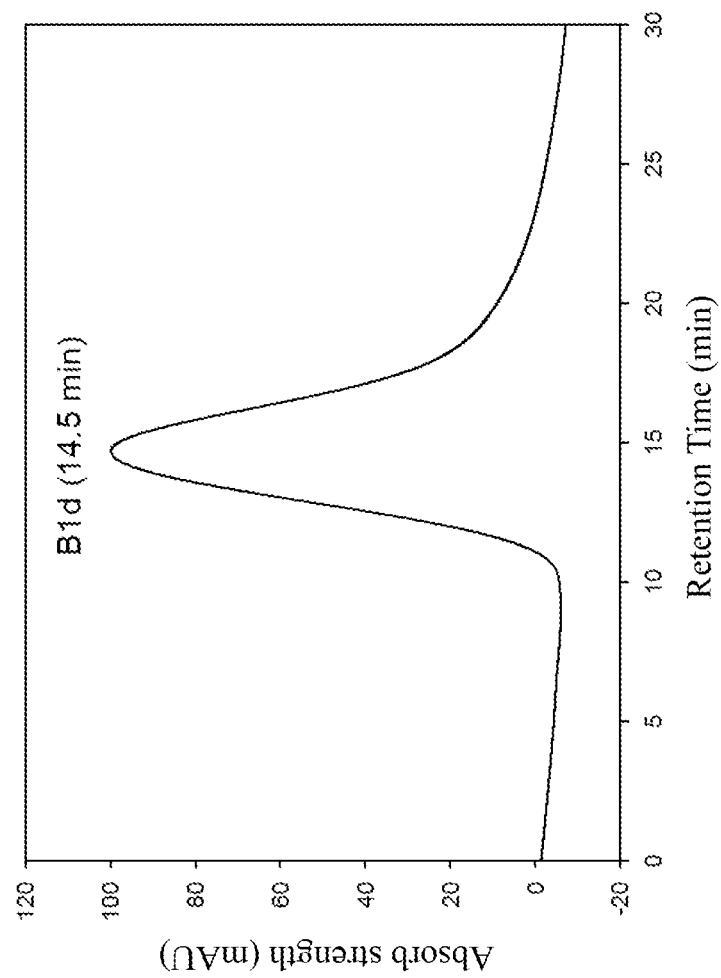
FIG. 7 shows the retention time of compound B1d in hydroxylapatite (HAp) column: the X-axis is retention time, the Y-axis is relative strength.
Figure 8:
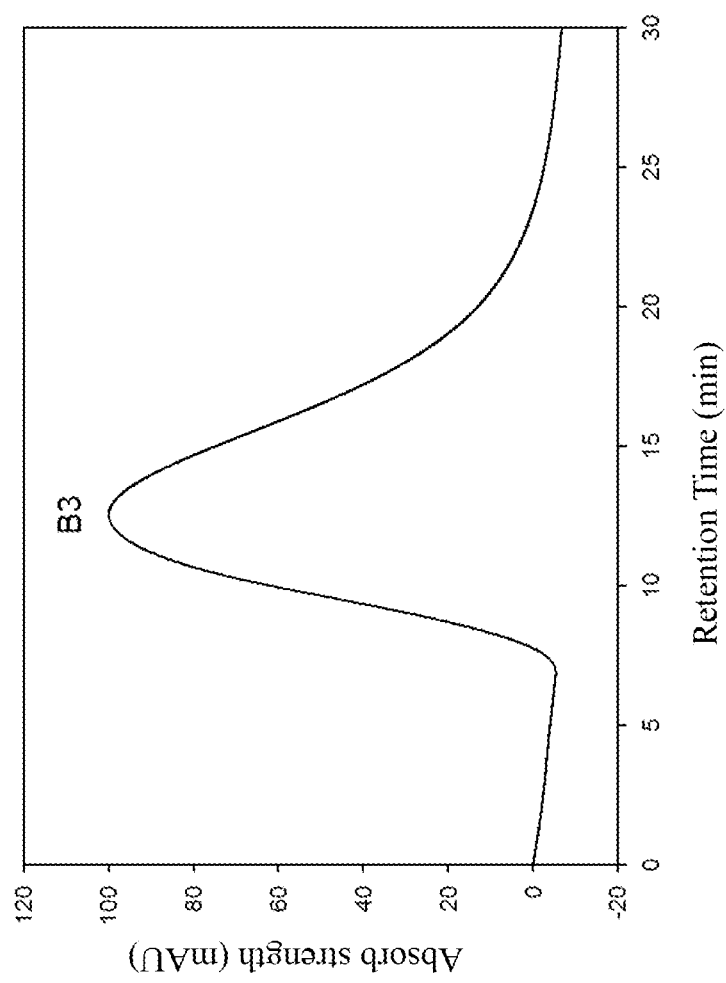
FIG. 8 shows the retention time of compound B3 in hydroxylapatite (HAp) column: the X-axis is retention time, the Y-axis is relative strength.

Using the column which is filling hydroxylapatite particles to evaluate the affinity. The diameter and length of hydroxylapatite column are 0.7 and 5 cm, and experimented by High Performance Liquid Chromatography system. The elute solution is 0.5 mM PBS (pH 7.4), the flow rate is 0.25 mL/min, and the wavelength is 220 nm. The retention time of each compound is shown in Table 1, and the chromatograms are shown in FIGS. 6-8.

Example 1

Prepared of Reference Component L1a

Rink amide resin (0.328 g, 0.2 mmole, load: 0.79 mmol/g) was weighted into the reaction vessel and swelled with freshly distilled DMF (5 mL) for 1 hr. After mixing with DEP solution for 5 minutes twice, resin was added 0.125 g Fmoc-Ala-OH (0.4 mmole), 0.208 g of PyBOP (0.4 mmole) and ACT reagent, then reacted for 30 minutes. After coupling was successful, CAP reagent was added and reacted for 25 minutes. Using the same dosage and steps to do the alanine addition for 5 times, then the time-consuming individually followed 40, 50, 60, 60 and 60 min for the conjugation of five residues of Ala. Removing the terminal Fmoc protection, Fmoc-Lys(Boc)-OH (0.187 g, 0.4 mmol) and PyBOP (0.208 g, 0.4 mmol) were added for the following coupling. After 90-minute reaction, to free the terminal amine, to react in CAP solution for 20 minutes, and to remove peptide from resin by used 95% trifluoro acetic acid and reacted for 2 hours, L1a peptide was obtained. Identified the purity by high performance liquid chromatography by used $C_{18}$ column, the mobile phase is 0.1% trifluoro acetic acid in methanol, the wavelength is 220 nm, the temperature is 25° C., and the flow rate is 0.4 mL/min. Single peak was present at 6.5 minutes in chromatography.

Example 2

Preparation of Reference Component L1b

Preloaded Glycine Wang resin (0.328 g) was weighted into the reaction vessel and swelled with freshly distilled DMF (5 mL) for 1 hr. DEP reagent was added to react for 5 minutes, the resin was added 0.165 g of Fmoc-Asp(tBu)-OH (0.4 mmole), 0.208 g of PyBOP (0.4 mmole) and ACT reagent, then the mixture was reacted for 30 minutes. After reaction completed, CAP reagent was added and further reacted for 25 minutes. Using the same dosage and steps to do the alanine addition for 5 times, then the time-consuming individually followed 40, 50, 60, 60 and 60 min for the conjugation of five residues of Asp. Removing the terminal Fmoc protection, Fmoc-Lys(Boc)-OH (0.187 g, 0.4 mmol) and PyBOP (0.208 g, 0.4 mmol) were added for the following coupling. After 90-minute reaction, to free the terminal amine, it reacted in CAP solution for 20 minutes, and to remove peptide from resin by used 95% trifluoroacetic acid and reacted for 2 hours, L1b peptide was obtained. The crude product was dissolved in a mixed solution (MeOH: $H_2O$:MeCN=2:1) and then purified by reverse phase medium pressure liquid chromatography, the flow rate of column is 0.5 mL/min. The purity was confirmed by high performance liquid chromatography, the column is $C_5$ column, the mobile phase is 0.1% of trifluoro acetic acid in methanol, the wavelength is 220 nm, the temperature of chromatography is 25° C. and the flow rate is 0.4 mL/min. Mass (MALDI-TOF): 788 (M+Na).

Example 3

Preparation of Compound L1c

Rink amide resin (0.328 g, 0.2 mmol) was weighted into the reaction vessel and swelled with freshly distilled DMF (5 mL) for 1 hr. DEP reagent was added to react for 5 minutes, then 0.119 g of Fmoc-Gly (0.4 mmole), 0.208 g of PyBOP (0.4 mmole) and ACT reagent were added and mixed for 30 minutes. After the reaction completed, CAP reagent was added and mixed for 25 minutes. Using the same dosage and steps to carry out glycine addition for twice, total reaction time are 45 minutes. Then, terminal Fmoc protection was removed before coupling with Fmoc-Asp(tBu)-OH (0.165 g, 0.4 mmole) for 50 minutes. Then, CAP reagent was added to complete the forth amino acid addition. Using the same dosage and steps to carry out glycine addition for twice, total reaction time are 60 minutes. After removed the terminal Fmoc, acetic anhydride was used to cap terminal amino groups. Trifluoroacetic acid was added to react for 2 hours to cleavage the linkage between peptide and resin. The crude peptide was dissolved in a mixed solution (MeOH:$H_2O$:MeCN=2:1:1) and purified by medium pressure liquid chromatography. Column is $C_{18}$ reversed-phase column and the flow rate is 0.5 mL/min. After identifying by $C_{18}$ reversed-phase thin-layer chromatography, a main product was obtained with 0.3 as retention factor. Identified the purity by high performance liquid chromatography, the column is $C_5$ column, the mobile phase is 0.1% trifluoroacetic acid in methanol, the wavelength is 220 nm, the temperature of chromatography is 25° C. and the flow rate is 0.4 mL/min. The retention time is 6.5 minutes.

Example 4

Preparation of Compound B1a

Rink amide resin (0.328 g) was weighted into the reaction vessel and swelled with freshly distilled DMF (5 mL) for 1 hr.

DEP reagent was added to react for 5 minutes, then 0.236 g of Fmoc-Lys(ivDde)-OH (0.4 mmole), 0.208 g of PyBOP (0.4 mmole) and ACT reagent were added and mixed for 40 minutes. After the reaction completed, CAP reagent was added and mixed for 25 minutes. Then, terminal Fmoc protection was removed before coupling with Fmoc-Lys(Fmoc)-OH (0.236 g, 0.4 mmole) for 70 minutes. Then, CAP reagent was added to complete the amino acid addition. Then, after removed two Fmoc protecting groups on the lysine, the resin was reacted with Fmoc-Asp(tBu)-OH (0.247 g, 0.6 mmole) and PyBOP (0.312 g, 0.6 mmole) for 60 minutes. Trifluoroacetic acid was added to react for 2 hours to cleavage the linkage between peptide and resin. The crude peptide was dissolved in a mixed solution (MeOH:$H_2O$=1:9) and purified by medium pressure liquid chromatography to obtain B1a. To analyze the purity by high performance liquid chromatography, $C_5$ reverse-phase column was used, the mobile phase is 0.1% trifluoro acetic acid in methanol, the wavelength is 220 nm, the temperature of chromatography is 25° C. and the flow rate is 0.4 mL/min, the retention time is 8.0 minutes.

Example 5

Preparation of Compound B1b

Rink amide resin (0.328 g) was weighted into the reaction vessel and swelled with freshly distilled DMF (5 mL) for 1 hr. DEP reagent was added to react for 5 minutes, then 0.236 g of Fmoc-Lys(ivDde)-OH (0.4 mmole), 0.208 g of PyBOP (0.4 mmole) and ACT reagent were added and mixed for 40 minutes, then 0.236 g of Fmoc-Lys(ivDde)-OH (0.4 mmole), 0.208 g of PyBOP (0.4 mmole) and ACT reagent were added and mixed for 40 minutes. After the reaction completed, CAP reagent was added and mixed for 25 minutes. Then, terminal Fmoc protection was removed before coupling with Fmoc-Lys(Fmoc)-OH (0.236 g, 0.4 mmole) for 70 minutes. Then, CAP reagent was added to complete the amino acid addition. Then, after removed two Fmoc protecting groups on the lysine, the resin was reacted with Fmoc-Asp(tBu)-OH (0.247 g, 0.6 mmole) and PyBOP (0.312 g, 0.6 mmole) for 60 minutes. Used the same steps, reagents and dosages to complete the aspartic acid addition for 80 minutes. Removed all Fmoc pretectors, and then used 95% trifluoro acetic acid to react for 2 hours to free B1b peptide from resin. The crude product was dissolved in MeOH:$H_2O$=3:7 mixed solution and separated by the $C_{18}$ reversed-phase column After identifying by $C_{18}$ reversed-phase thin-layer chromatography, obtained a single main product. Ethylation by acetic anhydride for 30 minutes and confirmed the color of ninhydrin is canary yellow, then obtained a B1b. The crude peptide was dissolved in a mixed solution (MeOH:$H_2O$=1:9) and purified by medium pressure liquid chromatography to obtain B1a. To analyze the purity by high performance liquid chromatography, $C_5$ reverse-phase column was used, the mobile phase is 0.1% trifluoro acetic acid in methanol, the wavelength is 220 nm, the temperature of chromatography is 25° C. and the flow rate is 0.4 mL/min, the retention time is 8.1 minutes.

Example 6

Preparation of Compound B1c

Figure 4:
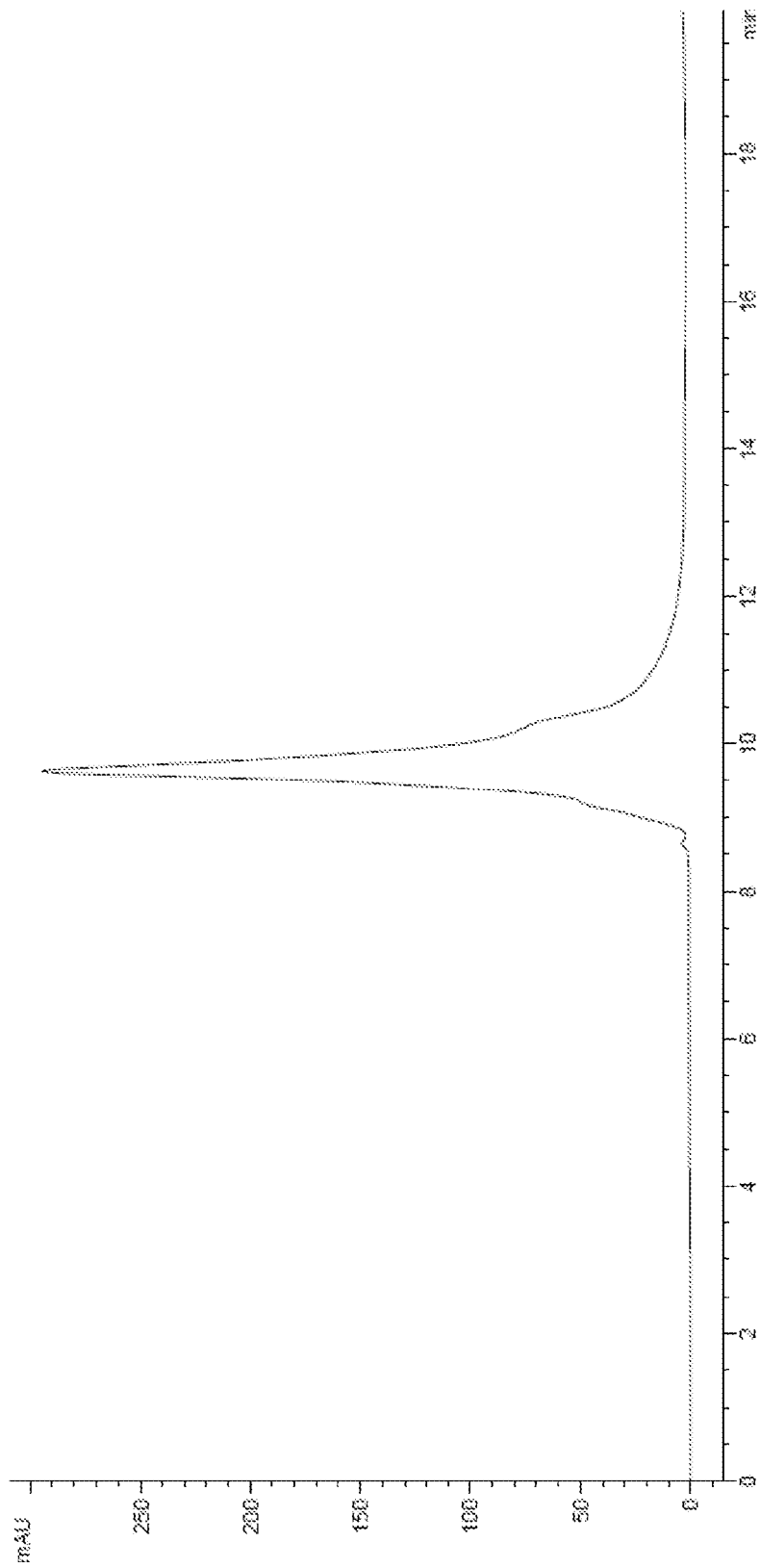
FIG. 4 shows the High Performance Liquid Chromatography (HPLC) of compound B1c: the X-axis is retention time, the Y-axis is relative strength, the elute solution is 0.1% trifluoro acetic acid (TFA) in methanol, the flow rate is 0.4 mL/min; the wavelength is 220 nm.

Rink amide resin (0.328 g) was weighted into the reaction vessel and swelled with freshly distilled DMF (5 mL) for 1 hr. DEP reagent was added to react for 5 minutes, then 0.236 g of Fmoc-Lys(ivDde)-OH (0.4 mmole), 0.208 g of PyBOP (0.4 mmole) and ACT reagent were added and mixed for 40 minutes. After the reaction completed, CAP reagent was added and mixed for 25 minutes. Then, terminal Fmoc protection was removed before coupling with Fmoc-Lys(Fmoc)-OH (0.236 g, 0.4 mmole) for 70 minutes. Then, CAP reagent was added to complete the amino acid addition. Then, after removed two Fmoc protecting groups on the lysine, Fmoc-Lys(Fmoc)-OH (0.354 g, 0.6 mmole) was conjugated by using the same coupling procedures, mount, but reaction time are 90 minutes. To remove all Fmoc protection, the resin was further reacted with Fmoc-Asp(tBu)-OH (0.329 g, 0.8 mmole) and PyBop (0.416 g, 0.8 mmole) for 90 minutes. After capping for 25 minutes, the second aspartic acid was conjugated on each branch by adding Fmoc-Asp(tBu)-OH (0.329 g, 0.8 mmole) and using the same procedures. The reaction time was 2 hr. At last, it removed the terminal Fmoc protecting group then added 1 mL acetic anhydride to react for 20 minutes. After ivDde protecting group was removed by using 4% dimethylhydrazine and reacted for 10 minutes. Trifluoroacetic acid was added to react for 2 hours to cleavage the linkage between peptide and resin. The crude product was dissolved in water again and purified by reverse phase HPLC, wherein the wavelength of UV detector is 220 nm, the flow rate is 0.5 mL/min, and obtained the desired product B1c. Its purity was determined by high performance liquid chromatography under 25° C., (FIG. 4) the column is $C_5$ reverse-phase column, the mobile phase is 0.1% trifluoro acetic acid in methanol, the wavelength is 220 nm, and the flow rate is 0.4 mL/min. The retention time is 9.6 minutes. Mass (MALDI-TOF) found 1740 (M+Na). $^1$H-NMR (400 MHz, acetone-$d_6$): δ 4.62 (m, 4H), 4.21 (m, 2H), 4.10 (m, 6H), 3.64 (s, 2H), 3.13 (m, 8H), 2.84 (m, 16H), 2.34 (s, 3H), 1.97 (s, 9H), 1.90 (s, 3H), 1.7 (m, 8H), 1.43 (m, 8H), 1.3 (m, 8H).

Example 7

Preparation of Compound B1d

Figure 5:
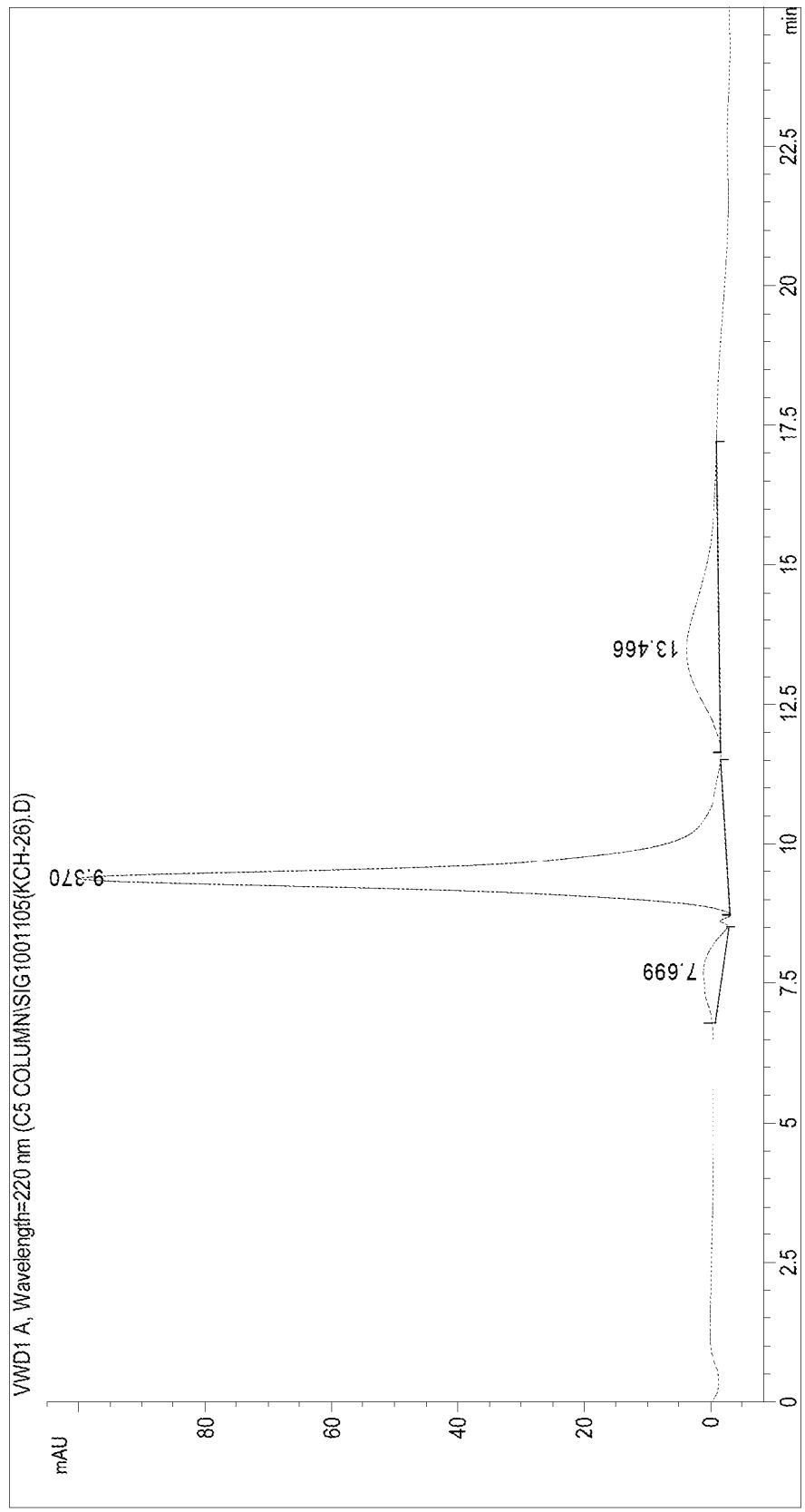
FIG. 5 shows the High Performance Liquid Chromatography (HPLC) of compound B1d: the elute solution is 0.1% trifluoro acetic acid (TFA) in methanol, the flow rate is 0.4 mL/min; the wavelength is 220 nm.

Rink amide resin (0.328 g) was weighted into the reaction vessel and swelled with freshly distilled DMF (5 mL) for 1 hr. DEP reagent was added to react for 5 minutes, then 0.236 g of Fmoc-Lys(ivDde)-OH (0.4 mmole), 0.208 g of PyBOP (0.4 mmole) and ACT reagent were added and mixed for 40 minutes. After the reaction completed, CAP reagent was added and mixed for 25 minutes. Then, terminal Fmoc protection was removed before coupling with Fmoc-Lys(Fmoc)-OH (0.236 g, 0.4 mmole) for 70 minutes. The same procedures were followed for further generation formation, but the amount of amino acid is two folds before. To remove all Fmoc protection, the resin was further reacted with Fmoc-Asp(tBu)-OH (0.412 g, 1.0 mmole) and PyBop (0.521 g, 1.0 mmole) for 120 minutes. After capping for 25 minutes, then added 1 mL acetic anhydride to react for 20 minutes. The ivDde protecting group was removed by using 4% dimethylhydrazine and reacted for 10 minutes. Trifluoroacetic acid was added to react for 2 hours to cleavage the linkage between peptide and resin. The crude product was dissolved in water again and purified by reverse phase HPLC, wherein the wavelength of UV detector is 220 nm, the flow rate is 0.5 mL/min, and obtained the desired product B1d. Its purity was determined by high performance liquid chromatography under 25° C., (FIG. 5) the column is $C_5$ reverse-phase column, the mobile phase is 0.1% trifluoro acetic acid in methanol, the wavelength is 220 nm, and the flow rate is 0.4 mL/min. Mass (MALDI-TOF) found 1740 (M+Na). The retention time is 9.4 minutes. $^1$H-NMR (400 MHz, $D_2O$): δ 4.60 (m, 6H), 4.16 (m, 8H), 3.92 (m, 2H), 3.62 (s, 2H), 3.11 (br, 16H), 2.77 (m, 16H), 1.96 (s, 24H), 1.88 (s, 3H), 1.68 (s, 16H), 1.42 (m, 14H), 1.28 (m, 18H).

Example 8

Preparation of Compound B1e

Rink amide resin (0.328 g) was weighted into the reaction vessel and swelled with freshly distilled DMF (5 mL) for 1 hr. DEP reagent was added to react for 5 minutes, then 0.481 g of Fmoc-Lys(ivDde)-OH (0.8 mmole), 0.416 g of PyBOP (0.8 mmole) and ACT reagent were added and mixed for 60 minutes. Coupling lysine on the peptide for 2 times as the steps aforesaid, and the reaction time are 90 and 120 minutes. After the reaction completed, CAP reagent was added and mixed for 20 minutes. Trifluoroacetic acid was added to react for 2 hours to cleavage the linkage between peptide and resin and to obtain B1e peptide.

Example 9

Preparation of Compound B2a

A mixture of PyBop (0.61 g, 0.5 mmole), Fmoc-Asp(tBu)-OH (0.206 g, 0.5 mmole) and ACT solution was reacted for 40 minutes. To the mixture was added the third generation of polyamindoamine dendrimer (0.053 g, 7.6 mmole) and 0.1 mL ethanol, then it was reacted for 5 hours under 200W, and the temperature set is 80° C. To remove the Fmoc protection, the crude product was added DEP solution and reacted for overnight. After removed the solvent, the solution was then reacted with 95% trifluoro acetic acid for 2 hours to remove Boc protection to give yellow residue. The crude product was dissolved in 10% dimethylsulfoxife and dialyzed is 5% aqueous methanol for 4 days by using membrane bag (MWCO 3500). After removed solvent, the oily crude was purified by gel exclusive chromatograpy using Sephadex G75 gel as stationary phase and water as mobile phase to obtain compound B2a as yellow oily after concentration. Its purity was determined by high performance liquid chromatography under 25° C., (FIG. 8) the column is $C_5$ reverse-phase column, the mobile phase is 0.1% trifluoro acetic acid in methanol, the wavelength is 220 nm, and the flow rate is 0.4 mL/min. The retention time is 4.7 minutes. $^1$H-NMR (200 MHz, $D_2$O): δ 4.10 (t, J=7 Hz, 17H), 3.55 (m, 74H), 3.26 (m, 64H), 3.05 (m, 80H), 2.80 (m, 78H), 2.43 (m, 43H), 2.25 (m, 44H).

Example 10

Preparation of Compound B2b

To follow the previous procedures in example 9, aspartic acid was conjugated on the sixth dendrimer to prepare compound B2a, but the reaction time is 9 hours. Its purity was determined by high performance liquid chromatography under 25° C., the column is $C_5$ reverse-phase column, the mobile phase is 0.1% trifluoro acetic acid in methanol, the wavelength is 220 nm, and the flow rate is 0.4 mL/min The retention time is 2.4 minutes.

Example 11

Preparation of Compound B3

First, the synthesis of L1b was reported example 2. After removed terminal Fmoc group on L1b, it was reacted with 4-carboxylbenzaldehyde (0.061 mg, 0.04 mmole) for 100 minutes and then capped the unreacted residues for 25 minutes. The third generation of polyamindoamine dendrimer (0.021 g, 0.1 mmole) was subjected and conjugated with the peptides on resin for 30 minutes. Then, sodium triacetoxyborohydride (0.315 g, 3 mmole) was added to reduce the imine linkage for 2 days until the reaction was completed. Trifluoroacetic acid was added to react for 2 hours to cleavage the linkage between peptide and resin to obtain yellow crude product. The crude was purified by gel exclusive chromatograpy using Sephadex G75 gel as stationary phase and water as mobile phase to obtain compound B3 as yellow oily after concentration. Its purity was determined by high performance liquid chromatography under 25° C., the column is $C_5$ reverse-phase column, the mobile phase is 0.1% trifluoro acetic acid in methanol, the wavelength is 220 nm, and the flow rate is 0.4 mL/min. The retention time is 7.8 minutes. $^1$H-NMR (400 MHz, $D_2$O): δ 7.72 (d, J=6 Hz, 32H), 7.43 (d, J=8 Hz, 32H), 4.11 (m, 96H), 3.89 (s, 48H), 3.28 (m, 276H), 2.83 (m, 192H), 1.14 (m, 208H).

There are more embodiments provided as follows.

Embodiment 1: A pharmaceutical composition, including a pharmaceutically acceptable carrier, and an effective amount a compound having one of components in formula 1A and formula 1B:

(1A)

and

(1B)

wherein U is one selected from a group consisting of -Lys, -Lys-(Asp-NHAc)$_J$, —NHAc, -Lys-(Asp-)$_K$-NHAc and (Asp-NHAc)$_J$, where J is one of 1 and 2, 20≥K≥1, and J and K are natural numbers, and Asp represents an aspartic acid, Lys represents a lysine, and Gly represents a glycine.

Embodiment 2: A pharmaceutical composition, including a pharmaceutically acceptable carrier, and an effective amount a compound having in formula 2:

(2)

wherein G is one selected from a group consisting of a polyamindoamine dendrimer (PAMAM), a polyester type dendrimer, a polyglycerol dendrimer, a triazine based dendrimer, a poly(propyleneimine)dendrimer, a Newkome-type dendrimers and a polylysine dendrimer, the sum of A and B is $(4×2^Y)$, where A, B and Y are natural numbers and Y is a number of generation, and Asp represents an aspartic acid.

Embodiment 3: A pharmaceutical composition, including a pharmaceutically acceptable carrier, and an effective amount of compound having a formula 3:

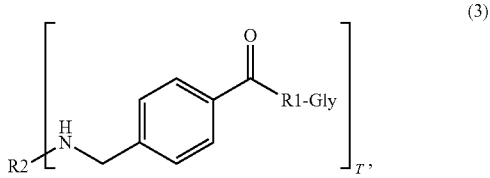

(3)

wherein R1 is -(Asp-)K, R2 is one selected from a group consisting of a polyamindoamine dendrimer (PAMAM), a polyester type dendrimer, a polyglycerol dendrimer, a triazine based dendrimer, a poly(propyleneimine)dendrimer and a Newkome-type dendrimers, where 64≥T≥1, 20≥K≥1, where T and K are natural numbers, and Asp represents an aspartic acid, and Gly represents a glycine.

Embodiment 4: A divergent compound, including a structure having one of a formula 1A and a formula 1B:

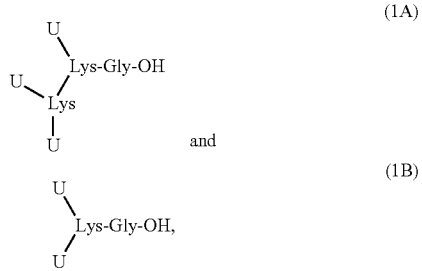

wherein U is one selected from a group consisting of -Lys, -Lys-(Asp-NHAc)$_J$, —NHAc, -Lys-(Asp-)$_K$-NHAc and (Asp-NHAc)$_J$, where J is one of 1 and 2, 20≥K≥1, J and K are natural numbers, Asp represents an aspartic acid, Lys represents a lysine, and Gly represents a glycine.

Embodiment 5: A divergent compound, including a structure having a formula 2:

wherein G is one selected from a group consisting of a polyamindoamine dendrimer (PAMAM), a polyester type dendrimer, a polyglycerol dendrimer, a triazine based dendrimer, a poly(propyleneimine)dendrimer, a Newkome-type dendrimers and a polylysine dendrimer, the sum of A and B is $(4 \times 2^Y)$, where A, B and Y are natural numbers and Y is a number of generation, and Asp represents an aspartic acid.

Embodiment 6: A divergent compound as claimed in embodiment 5, wherein G is the polyamindoamine dendrimer (PAMAM).

Embodiment 7: A divergent compound, including a structure having a formula 3:

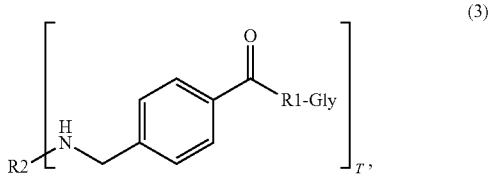

wherein R1 is -(Asp-)K, R2 is one selected from a group consisting of a polyamindoamine dendrimer (PAMAM), a polyester type dendrimer, a polyglycerol dendrimer, a triazine based dendrimer, a poly(propyleneimine)dendrimer and a Newkome-type dendrimers, where 64≥T≥1, 20≥K≥1, T and K are natural numbers, and Asp represents an aspartic acid, and Gly represents a glycine.

Embodiment 8: A divergent compound as claimed in embodiment 7, wherein R2 is the polyamindoamine dendrimer (PAMAM).

While the invention has been described in terms of what is presently considered to be the most practical and preferred embodiments, it is to be understood that the invention needs not be limited to the disclosed embodiments. Therefore, it is intended to cover various modifications and similar configuration included within the spirit and scope of the appended claims, which are to be accorded with the broadest interpretation so as to encompass all such modifications and similar structures.

REFERENCES

1. Hartgerink, J. D.; Beniash, E.; Stupp, S. I. Self-Assembly and Mineralization of Peptide-Amphiphile Nanofibers. *Science*, 2001, 294, 1684-1688.

2. Keum, D.-K.; Naka, K.; Chujo, Y. Effect of anionic polyamidoamine dendrimers on the crystallization of calcium carbonate by delayed addition method. *Bull. Chem. Soc. Jpn.* 2003, 76, 1687.

3. Wang, D.; Miller, S.; Sima, M.; Kopecková, P.; Kopecek, J. Synthesis and evaluation of water-soluble polymeric bone-targeted drug delivery systems. *Bioconjug Chem.* 2003, 14 (5), 853-859.

4. Wang, D.; Miller, S. C.; Shlyakhtenko, L. S.; Portillo, A. F.; Liu, X.-M.; Papangkorn, K.; Kopečková, P.; Lyubchenko, Y.; Higuchi, W. I.; Kopeček, J. Osteotropic Peptide That Differentiates Functional Domains of the Skeleton. *Bioconjugate Chem.* 2007, 18, 1375-1378.

5. Capriotti, L. A.; Beebe, Jr. T. P.; Schneider, J. P. Hydroxyapatite Surface-Induced Peptide Folding. *J. Am. Chem. Soc.* 2007, 129, 5283-5287.

6. George, A.; Veis, A. Phosphorylated Proteins and Control Over Apatite Nucleation, Crystal Growth, and Inhibition. *Chem. Rev.* 2008, 108, 4670-4693.

7. Rimola, A.; Corno, M.; Zicovich-Wilson, C. M.; Ugliengo, P. Ab Initio Modeling of Protein/Biomaterial Interactions: Glycine Adsorption at Hydroxyapatite Surfaces *J. Am. Chem. Soc.* 2008, 130, 16181-16183.

8. Zaupa, G.; Scrimin, P.; Prins, L. J. Origin of the Dendritic Effect in Multivalent Enzyme-Like Catalysts. *J. Am. Chem. Soc.* 2008, 130, 5699-5709.

9. Almora-Barrios, N.; Austen, K. F.; de Leeuw, N. H. Density Functional Theory Study of the Binding of Glycine, Proline, and Hydroxyproline to the Hydroxyapatite (0001) and (0110) Surfaces. *Langmuir* 2009, 25, 5018-5025.

10. Rosen, B. M.; Wilson, C. J.; Wilson, D. A.; Peterca, M.; Imam, M. R.; Percec, V. Dendron-Mediated Self-Assembly, Disassembly, and Self-Organization of Complex Systems. *Chem. Rev.* 2009, 109, 6275-6540.

11. Masica, D. L.; Schrier, S. B.; Specht, E. A.; Gray, J. J. De Novo Design of Peptide-Calcite Biomineralization Systems. *J. Am. Chem. Soc.* 2010, 132, 12252-12262.

What is claimed is:

1. A pharmaceutical composition, comprising a pharmaceutically acceptable carrier and an effective amount of a compound having a formula 3:

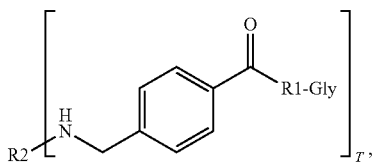

(3)

wherein R1 is -(Asp-)K, R2 is one selected from a group consisting of a polyamindoamine dendrimer (PAMAM), a polyester type dendrimer, a polyglycerol dendrimer, a triazine based dendrimer, a poly(propyleneimine)dendrimer and a Newkome-type dendrimer, where $64 \geq T \geq 1$, $20 \geq K \geq 1$, where T and K are natural numbers, Asp represents an aspartic acid, and Gly represents a glycine.

2. A divergent compound, comprising a structure having a formula 3:

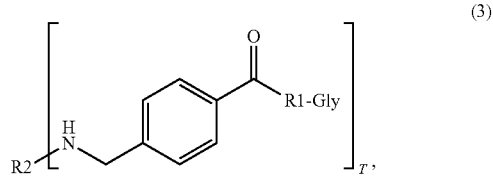

(3)

wherein R1 is -(Asp-)K, R2 is one selected from a group consisting of a polyamindoamine dendrimer (PAMAM), a polyester type dendrimer, a polyglycerol dendrimer, a triazine based dendrimer, a poly(propyleneimine)dendrimer and a Newkome-type dendrimer, where $64 \geq T \geq 1$, $20 \geq K \geq 1$, T and K are natural numbers, Asp represents an aspartic acid, and Gly represents a glycine.

3. A divergent compound as claimed in claim 2, wherein R2 is a polyamindoamine dendrimer (PAMAM).

* * * * *

SEQUENCE LISTING

```
<160> NUMBER OF SEQ ID NOS: 3

<210> SEQ ID NO 1
<211> LENGTH: 6
<212> TYPE: PRT
<213> ORGANISM: Artificial Sequence
<220> FEATURE:
<223> OTHER INFORMATION: L1a

<400> SEQUENCE: 1

Ala Ala Ala Ala Ala Ala
1               5

<210> SEQ ID NO 2
<211> LENGTH: 7
<212> TYPE: PRT
<213> ORGANISM: Artificial Sequence
<220> FEATURE:
<223> OTHER INFORMATION: L1b

<400> SEQUENCE: 2

Gly Asp Asp Asp Asp Asp Asp
1               5

<210> SEQ ID NO 3
<211> LENGTH: 6
<212> TYPE: PRT
<213> ORGANISM: Artificial Sequence
<220> FEATURE:
<223> OTHER INFORMATION: L1c

<400> SEQUENCE: 3

Gly Gly Gly Asp Asp Asp
1               5
```